United States Patent [19]

Lambert et al.

[11] Patent Number: 4,851,396
[45] Date of Patent: Jul. 25, 1989

[54] FUNGICIDAL COMPOSITIONS BASED ON NICOTINIC ACID DERIVATIVES, NEW NICOTINIC ACID DERIVATIVES AND PREPARATION THEREOF

[75] Inventors: Claude Lambert, Lyon; Regis Pepin, Rilleux-la-Pape, both of France

[73] Assignee: Rhone-Poulenc Agrochimie, Lyon, France

[21] Appl. No.: 50,487

[22] Filed: May 18, 1987

[30] Foreign Application Priority Data

May 16, 1986 [FR] France ............... 86 07260

[51] Int. Cl.$^4$ .............. A61K 31/455; C07F 7/02; C07D 213/84
[52] U.S. Cl. .................................. 514/63; 514/332; 514/344; 546/2; 546/3; 546/5; 546/14; 546/263; 546/286; 546/287
[58] Field of Search ............ 546/287, 286, 263, 2, 546/3, 5, 14; 514/344, 332, 63

[56] References Cited

PUBLICATIONS

Regitz et al., Chem. Abstracts: vol. 106, 196211u, (1987).
Fife et al., Chem. Abstracts: vol. 101, 54880j, (1984).
Sakamoto et al., Chem. Abstracts: vol. 103, 71164n, (1985).
Dunn, A. D., Chem. Abstracts: vol. 102, 6365u, (1985).

Primary Examiner—Mary C. Lee
Assistant Examiner—J. Richter
Attorney, Agent, or Firm—Burns, Doane, Swecker & Mathis

[57] ABSTRACT

Nicotinic acid derivatives
They are of formula:

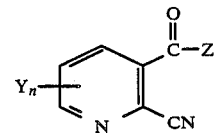

with:
Z=OR, with R=optionally substituted $C_1$–$C_{18}$-alkyl, $C_2$–$C_{18}$-alkenyl, $C_2$–$C_5$-alkynyl, phenyl or phenoxy;
Y=H, hal, $C_1$–$C_4$-alkyl or $C_1$–$C_4$-alkoxy and n=1 to 3.

Fungicidal products for agricultural use.

9 Claims, No Drawings

FUNGICIDAL COMPOSITIONS BASED ON NICOTINIC ACID DERIVATIVES, NEW NICOTINIC ACID DERIVATIVES AND PREPARATION THEREOF

The present invention relates to fungicidal compositions based on nicotinic acid derivatives, to new nicotinic acid derivatives and to the use of nicotinic acid derivatives in the control of fungal diseases of plants.

More particularly, the invention relates to fungicidal compositions which contain, as active substance, at least one compound of formula:

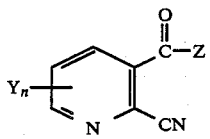

in which

Z is a radical OR in which

R is a hydrogen atom, an inorganic, metal or ammonium or organic cation M, especially substituted ammonium, in particular mono-, di- or trisubstituted with a straight-chain or branched alkyl radical containing 1 to 18 carbon atoms, a cycloalkyl radical containing 3 to 6 carbon atoms or a hydroxyalkyl radical containing 1 to 3 carbon atoms, or a straight-chain or branched alkyl radical containing 1 to 18 carbon atoms, or an alkenyl radical containing 2 to 18 carbon atoms, or an alkynyl radical containing 2 to 5 carbon atoms, it being possible for each of these radicals to be substituted with at least one substituent chosen from the group comprising:

a halogen atom and a cyano group, an alkoxy or alkylthio radical containing 1 to 4 carbon atoms, a phenoxy radical, optionally substituted with at least one substituent chosen from the group comprising a halogen atom, an alkyl radical containing 1 to 4 carbon atoms or an alkoxy radical containing 1 to 4 carbon atoms, and a group COOR' or OCOR', in which R' is an alkyl radical containing 1 to 4 carbon atoms, an alkenyl radical containing 2 to 4 carbon atoms or a phenyl radical, each of these alkyl, alkenyl or phenyl radicals being optionally substituted with at least one substituent chosen from the group comprising a halogen atom, an alkyl radical containing 1 to 4 carbon atoms or an alkoxy radical containing 1 to 4 carbon atoms, and a group I' of formula:

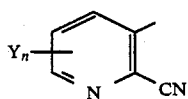

in which Y and n are as below, or a phenyl or naphthyl group, optionally substituted with at least one substituent chosen from the group comprising a halogen atom, an alkyl radical containing 1 to 4 carbon atoms, an alkoxy radical containing 1 to 4 carbon atoms and the radical $NO_2$, or an optionally substituted amino group, or a phenyl group, optionally substituted with at least one substituent chosen from the group comprising a halogen atom, an alkyl radical containing 1 to 4 carbon atoms and an alkoxy radical containing 1 to 4 carbon atoms, or a pyridylalkyl (containing 1 to 3 carbon atoms) group, optionally substituted with at least 1 halogen atom and/or an alkyl radical containing 1 to 4 carbon atoms and/or a cyano group, or an alkyl- or phenyl- or phenylalkylcarbonylalkyl group, each alkyl part of which contains 1 to 3 carbon atoms and the phenyl part of which is optionally substituted with 1 to 5 substituents chosen from the group comprising a halogen atom, an alkyl radical containing 1 to 4 carbon atoms, an alkoxy radical containing 1 to 4 carbon atoms and the radical $NO_2$, or a trialkyl($C_1$-$C_4$)silylalkyl($C_1$-$C_4$) group, it being possible for the alkyl part to be substituted with a phenyl group which may be optionally substituted with an alkyl radical containing 1 to 4 carbon atoms;

Y is a hydrogen or halogen atom, an alkyl or alkoxy radical containing 1 to 4 carbon atoms; and n is an integer from 1 to 3, with the possibility that, when n is greater than 1, Y may be identical or different.

Preferred compounds are of formula I in which R is a substituted ammonium, an optionally substituted alkyl radical containing 1 to 8 carbon atoms, more particularly methyl or ethyl, an alkenyl radical containing 2 to 4 carbon atoms, an alkoxycarbonylmethyl radical, an optionally substituted phenyl radical, an optionally substituted phenylcarbonylmethyl radical, or a pyridylmethyl radical.

Most of these compounds are original.

On the other hand, derivatives in the formulae of which Y=H and R is a hydrogen atom, a methyl or ethyl radical are known; however, their fungicidal properties have not been described.

The compounds which can be used according to the invention may be prepared according to methods known per se.

If, in formula I, radical R is an alkyl radical containing 1 to 4 carbon atoms, the products may be prepared according to a method known per se [cf. Bull. Soc. Chim. Belg. 89 205 (1980)] (method I) by reacting the appropriate alkyl chloroformate with the amido-carboxyl derivative of nicotinic acid derivatives according to the reaction scheme:

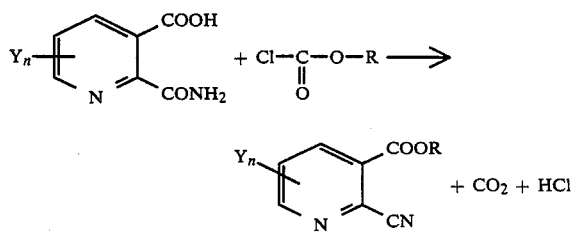

in a solvent medium, in the presence of an acceptor for acid. As solvent, there may be mentioned e.g. optionally halogenated aliphatic (especially methylene chloride) or aromatic hydrocarbons, ketones and nitriles. As acceptor for acid, there may be mentioned an inorganic base such as an alkali metal or alkaline earth metal carbonate or an organic base such as an amine of stronger basicity than that of the final product, especially a tertiary amine, e.g. triethylamine.

Derivatives of formula I in which R is a metal cation M may be prepared, in particular, when M is an alkali metal or alkaline earth metal atom, by the saponification of the corresponding ethyl or methyl ester with the metal hydroxide under consideration according to the reaction scheme (method II):

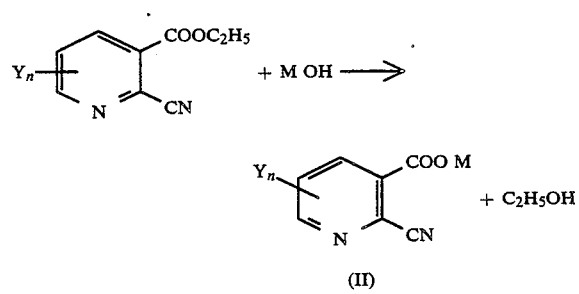

Derivatives of formula I in which R is neither an alkyl radical containing one to four carbon atoms nor a metal cation M may be prepared according to several methods (III): firstly, a compound of formula II may be reacted with an appropriate alkyl halide according to the reaction scheme (method IIIA):

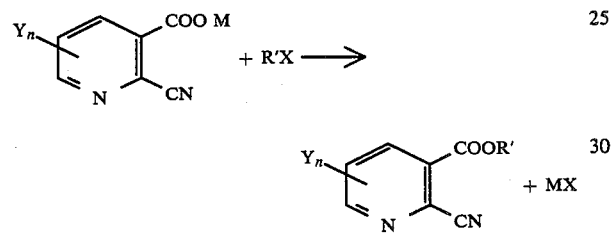

The reaction is carried out in an aliphatic or aromatic solvent medium such as e.g. optionally halogenated hydrocarbons (e.g. toluene), or amides, ketones or nitriles (e.g. acetonitrile). The reaction is advantageously carried out in the presence of a catalyst of the phase transfer catalyst type such as e.g. tris(3,6-dioxaheptyl)-amine (TDA-1) or crown ether 18-6.

A compound of formula II may also be reacted with a chlorinating agent to give an acid chloride derivative III which is reacted with an alcohol, according to the reaction scheme (method III B):

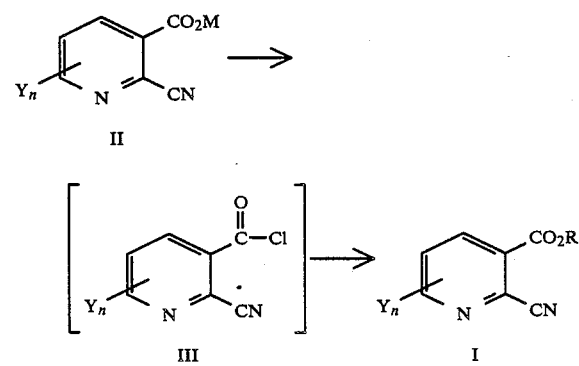

The treatment of II with a chlorinating agent, such as phosgene, oxalyl chloride or thionyl chloride, in an aliphatic solvent such as a chloroalkane gives derivative III. This is converted into compound I by reacting with the appropriate alcohol in the presence of an organic base such as e.g. pyridine.

A transesterification may also be carried out according to the reaction scheme (method III C):

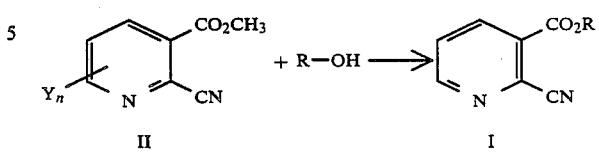

The reaction is carried out in an aromatic solvent such as e.g. toluene, in the presence of a catalytic quantity of a base such as sodium methylate, the methanol-solvent azeotrope being distilled as the methanol is being formed.

Products of formula I in which R is a substituted ammonium may be prepared by salification of the corresponding acid (R=H) with an appropriate amine (cf. Chem. Pharm. Bull. 27 2473 (1979)] (method IV).

The following examples illustrate the preparation of the compounds according to the invention and their fungicidal properties. The structure of these compounds was verified by NMR spectrography.

Example 1: Potassium 2-cyanonicotinate (compound 3)

Ethyl 2-cyanonicotinate (compound 2) (20 g; 0.113 mol) is added to a solution of potassium hydroxide (6 g; 0.017 mol) in distilled water (150 cc). The mixture is then allowed to stand for 10 hours at 25° C., and then washed with ether (2×50 cc). The aqueous solution is then evaporated to dryness to give compound 3 (19.1 g; m.p. 300° C.).

Example 2: Octyl 2-cyanonicotinate (compound 6)

Compound 3 (4.1 g; 0.022 mol), octyl bromide (3.86 g; 0.02 mol) and crown ether 18-6 (130 mg; 0.0005 mol) are added to acetonitrile (40 cc). The reaction mixture is heated under reflux for 4 hours. The solvent is then evaporated off and the residue taken up with water and then extracted with dichloromethane. After drying, evaporation and then purification on a silica column, a yellow oil (3.9 g) is obtained (yield=75%).

Example 3: (Ethoxycarbonyl)methyl 2-cyanonicotinate (compound 2)

Toluene (40 cc) containing compound 3 (4.1 g; 0.022 mol), ethyl bromoacetate (3.35 g; 0.02 mol) and TDA-1 (0.3 cc) is heated under reflux for 4 hours. The toluene is then evaporated off and the residue taken up with water and then extracted with dichloromethane. After drying, evaporating and crystallization in pentane, (ethoxycarbonyl)-methyl 2-cyanonicotinate (4.7 g; m.p. 74°. C.) is obtained.

Example 4: Diisopropylammonium 2-cyanonicotinate (compound 31)

2-Cyanonicotinic acid (0.74 g; 0.005 mol) suspended in acetone (40 cc) is treated with diisopropylamine (0.56 g; 0.0056 mol). The solvent is then evaporated off and the residue is crystallized in hexane: diisopropylammonium 2-cyanonicotinate (1.24 g; m.p. 156.7° C.) is obtained (yield=99%).

Example 5: 2,2,2-Trichloroethyl 2-cyanonicotinate (compound 63)

Oxalyl chloride (2.8 g; 0.022 mol) is added to a suspension of compound 3 (4.1 g; 0.022 mol) in dichloromethane (50 cc). The mixture is heated under reflux until gas evolution ceases and then treated with a solution of trichloroethanol (3.3 g; 0.022 mol) and pyridine (3.5 g; 0.044 mol) in dichloromethane (30 cc). The mixture is then treated with water and then dried. After evaporation of the solvent and crystallization in pentane, 2,2,2-tri-chloroethyl 2-cyanonicotinate (4.55 g; m.p. 103° C.) is obtained (yield=78%).

Example 6: 2-(2-Pyridyl)ethyl 2-cyanonicotinate (compound 84)

A solution of methyl 2-cyanonicotinate (8.1 g; 0.05 mol) and 2-pyridylethanol (7.4 g; 0.06 mol) in toluene (300 cc) is treated with sodium methylate (0.3 g; 0.005 mol). The methanol-toluene azeotrope is distilled off and the toluene is then evaporated off. The residue is treated with water. The precipitate formed is filtered, dried and then washed with pentane. Compound 84 (9.64 g; m.p. 73.5° C.) is obtained (yield=76%).

Example 7

Operating according to the procedure in Examples 2 and 6, the following compounds are obtained, the formulae and the physicochemical properties of which are given in the following table:

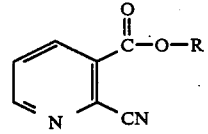

| | R | m.p. °C. | Method |
|---|---|---|---|
| 1 | CH₃ | 82,9 | I |
| 2 | C₂H₅ | 41 | II |
| 3 | K | 300 | II |
| 4 | isoC₃H₇ | 92 | III A |
| 5 | nC₅H₁₁ | oil | III A, B |
| 6 | nC₈H₁₇ | 25 (oil) | III A |
| 7 | —CH₂—CH=CH₂ | oil | III A |
| 8 | —CH₂—CH=CH—Cl | 59,5 | III A |
| 9 | CH₂—CH=CH—CH₃ (E) | oil | III A |
| 10 | CH₂—C≡CH | 112 | III A |
| 11 | CH₂—C₆H₅ (benzyl) | 67 | III A |
| 12 | CH₂—C₆H₄—Br | 116 | III A |
| 13 | CH₂—C₆H₃Cl₂ | 165 | III A |
| 14 | CH₂—(pyridyl) | 91 | III A |
| 15 | CH₂—C(=O)—CH₃ | 86 | III A |
| 16 | CH₂—C(=O)—C₆H₅ | 115 | III A |
| 17 | CH₂—C(=O)—C₆H₄—CH₃ | 142 | III A |

| | R | m.p. °C. | Method |
|---|---|---|---|
| 18 | CH₂−C(=O)−C₆H₄−Br (4-Br) | 162 | III A |
| 19 | CH₂−C(=O)−C₆H₄−Cl (4-Cl) | 140.5 | III A |
| 20 | CH₂−C(=O)−C₆H₃−Cl₂ (3,4-diCl) | 140 | III A |
| 21 | CH₂−C(=O)−O−CH₃ | 116 | III A |
| 22 | CH₂−C(=O)−OC₂H₅ | 74 | III A |
| 23 | −CH(CH₃)−C(=O)−OC₂H₅ | 40 | III A |
| 24 | −CH(C₂H₅)−C(=O)−OC₂H₅ | 60 | III A |
| 25 | −(CH₂)₃−C(=O)−OC₂H₅ | 60.5 | III A |
| 26 | −CH₂−CH=CH−C(=O)−OCH₃ (E) | 93.5 | III A |
| 27 | CH₂−CN | 64 | III A |
| 28 | −CH₂−CH=CH−CH₂−O−C(=O)−(3-CN-pyridin-4-yl) | 209 | III A |
| 29 | −CH₂−C₆H₄−CH₂−O−C(=O)−(3-CN-pyridin-4-yl) | 242 | III A |
| 30 | HN⁺(C₂H₅)₃ | 65 | IV |
| 31 | H₂N⁺(CH(CH₃)₂)₂ | 157 | IV |
| 32 | H₂N⁺(c-C₆H₁₁)₂ | 178 | IV |
| 33 | H₂N⁺(CH₂CH₂OH)₂ | 115 | IV |
| 34 | H₃N⁺(CH₂)₁₇CH₃ | 79 | IV |
| 35 | H | 171 | 1 |
| 36 | CH₂CH₂−O−C₆H₅ | 102 | III A |
| 37 | CH₂CH₂−O−C₆H₄−Br | 71 | III A |

-continued

| | R | m.p. °C. | Method |
|---|---|---|---|
| 38 | CH$_2$CH$_2$Br | 65 | III A |
| 39 | CH$_2$-(2,6-dichloropyridin-4-yl) | 161.5 | III A |
| 40 | CH$_2$-C$_6$H$_4$-4-NO$_2$ | 202 | III A |
| 41 | CH$_2$-C$_6$H$_4$-4-Cl | 133 | III A |
| 42 | CH$_2$-C$_6$H$_4$-3-NO$_2$ | 156.5 | III A |
| 43 | CH$_2$-C$_6$H$_4$-4-CH$_3$ | 97.5 | III A |
| 44 | CH$_2$-C$_6$H$_2$-2,3,4-Cl$_3$ | 179 | III A |
| 45 | CH$_2$CO$_2$C(CH$_3$)$_3$ | 47 | III A |
| 46 | CH$_3$-C$_6$H$_4$-3-Cl | 112 | III A |
| 47 | CH$_2$-C$_6$H$_4$-2-Cl | 126 | III A |
| 48 | CH$_2$-C$_6$H$_3$-2,4,5-Cl$_3$ | 102 | III A |
| 49 | CH$_2$-(pyridin-2-yl) | 106.5 | III A, C |

-continued

| | R | m.p. °C. | Method |
|---|---|---|---|
| 50 | CH$_2$-C(=O)-(2,4-dichlorophenyl) | 161.5 | III A |
| 51 | C$_4$H$_9$ | oil | III A |
| 52 | CH$_2$-(4-pyridyl) | 100 | III A |
| 53 | CH$_2$-C(=O)-OCH$_2$CH=CHCH$_3$ | 123 | III A |
| 54 | CH$_2$-Si(CH$_3$)$_2$-CH$_2$C$_6$H$_5$ | oil | III A |
| 55 | CH$_2$-Si(CH$_3$)$_2$-CH$_2$-(4-C(CH$_3$)$_3$-phenyl) | oil | III A |
| 56 | CH(CO$_2$C$_2$H$_5$)$_2$ | 93 | III A |
| 57 | CH$_2$-(4-bromophenyl) | 157 | III A |
| 58 | CH$_2$-(3-fluorophenyl) | 168 | III A |
| 59 | CH$_2$-(2-fluoro-6-chlorophenyl) | 151 | III A |
| 60 | CH$_2$-(2-methylphenyl) | 112 | III A |
| 61 | CH$_2$-(2-iodophenyl) | 135 | III A |
| 62 | CH$_2$-CF$_3$ | 80.5 | III B |
| 63 | CH$_2$CCl$_3$ | 103 | III B |
| 64 | CH$_2$CHCl$_2$ | 83.5 | |

-continued

| | R | m.p. °C. | Method |
|---|---|---|---|
| 65 | 2,4,6-trimethylbenzyl (CH₂-C₆H₂(CH₃)₃) | 251 | III A |
| 66 | 3-methylbenzyl | 76 | III A |
| 67 | 4-tert-butylbenzyl | 71 | III A |
| 68 | 4-fluorobenzyl | 108 | III A |
| 69 | 2,4-dichlorobenzyl | 151 | III A |
| 70 | $CH_2-CH(C_2H_5)-C_4H_9$ | oil | III B |
| 71 | 2-nitrobenzyl | 160 | III A |
| 72 | 3,4-dichlorobenzyl | 162 | III A |
| 73 | 2-chloro-4-nitrobenzyl | 124 | III A |
| 74 | $(CH_2)_{15}CH_3$ | 108 | III B |
| 75 | 3,4-dichlorophenyl | 145.5 | III B |
| 76 | 4-chlorophenyl | 125 | III B |

-continued

| | R | m.p. °C. | Method |
|---|---|---|---|
| 77 | 3-Cl-C₆H₄- | 139.5 | III B |
| 78 | 2-Cl-C₆H₄- | 121 | III B |
| 79 | 2,5-Cl₂-C₆H₃- | 130 | III B |
| 80 | 4-Br-C₆H₄- | 110.5 | III B |
| 81 | 2,3-Cl₂-C₆H₃- | 164.5 | III B |
| 82 | 4-OCH₃-C₆H₄- | 122 | III B |
| 83 | $(CH_2)_{11}CH_3$ | 52 | IV B |
| 84 | $CH_2CH_2$-(2-pyridyl) | 73.5 | III C |
| 85 | 2-F-C₆H₄-CH₂- | 113 | III A |
| 86 | $CH_2CH_2-SC_2H_5$ | oil | III B |
| 87 | $CH_2CH_2-I$ | 48 | III B |
| 88 | $C_3H_7$ | oil | III B |
| 89 | $CH_2CH(CH_3)_2$ | oil | III B |
| 90 | 3-OCH₃-C₆H₄-CH₂- | 83.5 | III A |
| 91 | $CH_2CH_2Cl$ | 69 | III B |
| 92 | $C(CH_3)_3$ | 62 | III B |

-continued

| R | m.p. °C. | Method |
|---|---|---|
| 93    CH$_2$—(naphthyl) | 140 | III B |

Example 6: Glasshouse test on *Piricularia oryzae*

10 cm-high rice seedlings (variety Marcheti rosa), gathered in troughs containing 2 each, are treated, by irrigating the soil, with an aqueous suspension containing:

30 mg of the product to be tested;
15 mg of surfactant, a condensate of ethylene oxide (20 mol) with sorbitan monooleate, and
water qs 30 cc.

This suspension, applied to 7 cm-sided square pots, corresponds to a dose of approximately 60 kg/ha of active substance. The product is allowed to be absorbed by the soil. A part of the rice seedlings has not been treated so as to use it as control. 24 hours after the treatment, all the rice seedlings are inoculated with a suspension of *Piricularia oryzae* spores obtained by scraping an in vitro culture, by spraying on the leaves at a rate of 5 cc of the suspension per pot. The pots are incubated for 48 h at 25° C. at 100% relative humidity.

Observations are made 48 h after the inoculation.

Under these conditions, it is observed that at a dose of 1000 ppm an inhibition of at least 80% of the fungus is obtained with compounds 1 to 9, 11, 12, 14 to 18 and 20 to 27, 30 to 32, 35, 36, 38, 40, 42 to 45, 47 to 50, 52, 69 to 71, 73, 74 and 77 to 82.

These results demonstrate clearly the properties of the compounds according to the invention as systemic fungicides and their remarkable effect on the *Piricularia* disease of rice.

These compositions may also contain any other type of ingredient, e.g. protective colloids, adhesives, thickeners, thixotropic agents, penetrants, stabilizers, sequestering agents and the like, as well as other known active substances having pesticidal properties (especially insecticidal or fungicidal properties) or properties which promote plant growth (especially fertilizers) or plant growth regulating properties. More generally, the compounds according to the invention may be combined with all the solid or liquid additives which correspond to the customary techniques of formulation.

In the case where the compounds according to the invention are used as fungicides, these doses for use may vary within wide limits, especially depending on the virulence of the fungi and the climatic conditions.

In general, compositions containing 0.5 to 5000 ppm of active substance are well suited; these values are given for compositions ready for application. ppm means "parts per million". The range from 0.5 to 5000 ppm corresponds to a range from $5 \times 10^{-5}$ to 0.5% (percentages by weight).

As regards compositions suitable for storage and for transport, they more advantageously contain from 0.5 to 95% (by weight) of active substance.

Thus, the compositions for agricultural use according to the invention may therefore contain active substances according to the invention within very wide limits, ranging from $5 \times 10^{-5}\%$ to 95% (by weight).

As already stated, the compounds according to the invention are generally present in combination with carriers and optionally with surfactants.

In the present account, the term "carrier" denotes an organic or inorganic, natural or synthetic material which is in combination with the active substance to facilitate its application to the plant, seeds or soil. This carrier is therefore generally inert, and it must be acceptable in agriculture, especially on the plant treated. The carrier may be solid (clays, natural or synthetic silicates, silica, resins, waxes, solid fertilizers and the like) or liquid (water, alcohols, ketones, petroleum fractions, aromatic or paraffinic hydrocarbons, chlorinated hydrocarbons, liquefied gases and the like).

The surfactant may be an emulsifier, dispersant or wetting agent of the ionic or the nonionic type. There may be mentioned e.g. salts of polyacrylic acids, salts of lignosulphonic acid, salts of phenolsulphonic or naphthalenesulphonic acids, polycondensates of ethylene oxide with fatty alcohols or fatty acids or fatty amines, substituted phenols (especially alkylphenols or arylphenols), salts of sulphosuccinic acid esters, taurine derivatives (especially alkyltaurates), and phosphoric acid esters of polycondensates of ethylene oxide with alcohols or phenols. The presence of at least one surfactant is generally essential when the active substance and/or the inert carrier are not water-soluble and the vector agent for the application is water.

The compositions used in the invention may be in fairly diverse, solid or liquid forms.

As solid forms of composition, there may be mentioned powders for dusting (with a content of active substances which may range up to 100%).

As liquid forms of composition, or forms designed to constitute liquid compositions when applied, there may be mentioned solutions, especially water-soluble concentrates, emulsifiable concentrates, emulsions, flowables, aerosols, wettable powders (or powder for spraying), granules and pastes.

The emulsifiable or soluble concentrates most frequently contain 10 to 80% of active substance, whereas the emulsions or solutions ready for application, for their part, contain 0.001 to 20% of active substance. In addition to the active substance and the solvent, the emulsifiable concentrates may contain, when required, a suitable co-solvent and from 2 to 20% of suitable additives such as stabilizers, surfactants, especially emulsifiers, penetrants, corrosion inhibitors, colourings and adhesives.

From these concentrates, by dilution with water, it is possible to obtain emulsions of any desired concentration which are especially suitable for application to crops.

Flowables, which may also be applied by spraying, are prepared so as to obtain a stable fluid product which does not settle, and they usually contain from 10 to 75% of active substance, from 0.5 to 15% of surfactants, from 0.1 to 10% of thixotropic agents, from 0 to 10% of suitable additives such as antifoams, corrosion inhibitors, stabilizers, penetrants and adhesives and, as a carrier, water or an organic liquid in which the active substance is of low solubility or insoluble: some solid organic substances or inorganic salts may be dissolved in the carrier to assist in preventing sedimentation or as antifreeze for the water.

By way of example, the composition of several aqueous suspensions according to the invention is as follows:

Example A

An aqueous suspension containing the following is prepared:

| | |
|---|---|
| active substance (compound no. 4) | 500 g/l |
| wetting agent (polycondensate of $C_{13}$ synthetic alcohol and ethylene oxide) | 10 g/l |
| dispersant (salified phosphate of polycondensate of arylphenol with ethylene oxide) | 50 g/l |
| antifreeze (propylene glycol) | 100 g/l |
| thickener (polysaccharide) | 1.6 g/l |
| biocide (sodium 4-hydroxymethylbenzoate) | 3.3 g/l |
| water qs | 1 liter |

Example B-aqueous suspension

An aqueous suspension containing the following is prepared:

| | |
|---|---|
| active substance (compound no. 7) | 100 g/l |
| wetting agent (alkylphenol/ethylene oxide polycondensate) | 5 g/l |
| dispersant (Na naphthalenesulphonate) | 10 g/l |
| antifreeze (propylene glycol) | 100 g/l |
| thickener (polysaccharide) | 3 g/l |
| biocide (formaldehyde) | 1 g/l |
| water qs | 1 liter |

Example C-aqueous suspension

An aqueous suspension containing the following is prepared:

| | |
|---|---|
| active substance (compound no. 22) | 250 g/l |
| wetting agent ($C_{13}$ synthetic alcohol/ethylene oxide polycondensate) | 10 g/l |
| dispersant (sodium lignosulphonate) | 15 g/l |
| antifreeze (urea) | 50 g/l |
| thickener (polysaccharide) | 2.5 g/l |
| biocide (formaldehyde) | 1 g/l |
| water qs | 1 liter. |

The wettable powders (or powder for spraying) are usually prepared so as to contain 20 to 95% of active substance, and they usually contain, in addition to the solid carrier, from 0 to 5% of a wetting agent, from 3 to 10% of a dispersant and, when required, from 0 to 10% of one or more stabilizers and/or other additives such as penetrants, adhesives, or anticaking agents, colourings and the like.

By way of example, the composition of several wettabe powders is as follows:

| | |
|---|---|
| active substance (compound no. 1 according to the invention) | 50% |
| fatty alcohol/ethylene oxide condensate (wetting agent) | 2.5% |
| styrylphenol/ethylene oxide condensate (dispersant) | 5% |
| chalk (inert carrier) | 42.5% |

Example E-10% wettable powder

| | |
|---|---|
| active substance (compound no. 4) | 10% |
| branched type $C_{13}$ oxosynthetic alcohol/ethylene oxide condensate, containing 8 to 10 units of ethylene oxide (wetting agent) | 0.75% |
| neutral calcium lignosulphonate (dispersant) | 12% |
| calcium carbonate (inert filter) qs | 100% |

Example F-75% wettable powder containing the same ingredients as in the previous example, in the following proportions

| ingredients as in the previous example, in the following proportions: | |
|---|---|
| active substance (compound no. 7) | 75% |
| wetting agent | 1.50% |
| dispersant | 8% |
| calcium carbonate (inert filler) qs | 100% |

Example G-90% wettable powder

| | |
|---|---|
| active substance (compound no. 22) | 90% |
| fatty alcohol/ethylene oxide condensate (wetting agent) | 4% |
| styrylphenol/ethylene oxide condensate (dispersant) | 6% |

Example H-50% wettable powder

| | |
|---|---|
| active substance (compound no. 4 according to the invention) | 50% |
| mixture of anionic and nonionic surfactants (wetting agent) | 2.5% |
| neutral sodium lignosulphonate (dispersant) | 5% |
| kaolin clay (inert carrier) | 42.5% |

In order to obtain these powders for spraying or wettable powders, the active substance is intimately mixed in suitable mixers with additional substances and the mixtures are ground in suitable mills or other grinders. Powders for spraying, the wettability and suspendability of which are advantageous, are thereby obtained; they may be suspended in water at any desired concentration and this suspension may very advantageously be used, especially for application to plant leaves.

The compounds according to the invention may advantageously be formulated in the form of water-dispersible granules which are also included within the scope of the invention.

These dispersible granules, with an apparent density generally between 0.3 and 0.6, have a particle size generally between approximately 150 and 2,000 and preferably between 300 and 1,500 microns.

The active substance content of these granules is generally between approximately 1% and 90%, and preferably between 25% and 90%.

The remaining part of the granules essentially consists of a solid filler and, if required, surfactant adjuvants which give water dispersibility properties to the granules. These granules may essentially be of two distinct types depending on whether the filler used is soluble or insoluble in water. When the filler is water-soluble, it may be inorganic or preferably organic. Excellent results were obtained with urea. In the case of an insoluble filler, the latter is preferably inorganic, such as e.g. kaolin or bentonite. It is then accompanied by surfactants (at a rate of 2 to 20% by weight of the granules), more than half of which surfactant consists of at least one essentially anionic dispersant such as a poly(alkali metal or alkaline earth metal naphthalenesulphonate) or an alkali metal or alkaline earth metal lignosulphonate, the remaining part consisting of nonionic or anionic wetting agents such as an alkali metal or alkaline earth metal alkyl naphthalenesulphonate.

Moreover, other adjuvants such as antifoams may be added, although they are not indispensable.

The granules according to the invention may be prepared by mixing the necessary ingredients followed by granulation according to several techniques known per se (pelletizer, fluidized bed, atomizer, extrusion and the like). The process generally ends with a crushing followed by sieving to the particle size chosen within the limits mentioned above.

It is preferably produced by extrusion, operating as indicated in the examples below.

Example I-Dispersible granules with 90% active substance concentration

90% by weight of active substance (compound no. 7) and 10% of urea pellets are mixed in a mixer. The mixture is then ground in a toothed roll crusher. A powder is obtained, which is moistened with approximately 8% by weight of water. The moist powder is extruded in a perforated rotor extruder. Granules are obtained, which are dried and then crushed and sieved, so as to retain only the granules with a size between 150 and 2,000 microns respectively.

Example J-Dispersible granules with a 75% active substance concentration

The following constituents are mixed in a mixer:

| active substance (compound no. 22) | 75% |
|---|---|
| wetting agent (sodium alkyl naphthalene-sulphonate) | 2% |
| dispersant (sodium naphthalenepolysulphonate) | 8% |
| water-insoluble inert filler (kaolin) | 15% |

This mixture is granulated in a fluidized bed, in the presence of water, and then dried, crushed and sieved so as to obtain granules of size between 0.16 and 0.40 mm.

These granules may be used alone, in solution or dispersion in water so as to obtain the dose sought. They may also be used to prepare combinations with other active substances, especially fungicides, the latter being in the form of wettable powders or granules or aqueous suspensions.

As already stated, the dispersions and aqueous emulsions, e.g. compositions obtained by diluting with water a wettable powder or an emulsifiable concentrate according to the invention, are included within the general scope of the compositions which can be used in the present invention. The emulsions may be of the water-in-oil or oil-in-water type, and they may have a thick consistency like that of a "mayonnaise".

The invention further relates to a method for the treatment of crops against diseases caused by phytopathogenic fungi which belong to very different families and especially against strains of *Botrytis sp* which are sensitive or resistant to benzimidazoles, eyespot (strains sensitive or resistant to benzimidazoles), seedborne fungi such as *Pythium sp, Fusarium sp, Septoria sp, Rhizoctonia sp* or fungi responsible for rots such as *Monilia sp, Penicillium sp, Rhizopus sp* or *Venturia sp, Phytophthora sp* and the like.

This method consists in applying to these crops an effective amount of a composition containing a compound according to formula (I) as the active substance. "Effective amount" means a quantity sufficient to enable the fungi present on these crops to be controlled or destroyed. However, the doses for use may vary within wide limits depending on the fungus to be controlled, the type of crop and the climatic conditions, and depending on the compound used.

In practice, doses ranging from 1 g/hl to 500 g/hl, which correspond substantially to doses of active substance per hectare of approximately 10 g/ha to 5000 g/ha, generally give good results.

We claim:

1. A nicotinic acid derivative of formula:

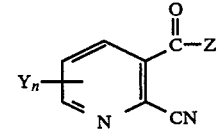

in which

Z is a radical OR in which

R is (1) a hydrogen atom, alkali metal or alkaline earth metal or optionally substituted ammonium or organic cation M, or (2) a straight-chain or branched alkyl radical containing 1 to 18 carbon atoms, or an alkenyl radical containing 2 to 18 carbon atoms, or an alkynyl radical containing 2 to 5 carbon atoms, it being possible for each of these radicals to be substituted with at least one of:

(A) a halogen atom or a cyano group, (B) an alkoxy or alkylthio radical containing 1 to 4 carbon atoms, (C) a phenoxy radical, optionally substituted with at least one of a halogen atom, an alkyl radial containing 1 to 4 carbon atoms or an alkoxy radical containing 1 to 4 carbon atoms, and (D) a group COOR' or OCOR', in which R' is an alkyl radical containing 1 to 4 carbon atoms, an alkenyl radical containing 2 to 4 carbon atoms or a phenyl radical, (each of these alkyl, alkenyl or phenyl radicals being optionally substituted with at least one of a halogen atom, an alkyl radical containing 1 to 4 carbon atoms or an alkoxy radical containing 1 to 4 carbon atoms), or a group I' of formula:

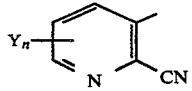

in which Y and n are as below,
- (E) a phenyl or naphthyl group, optionally substituted with at least one of a halogen atom, an alkyl radical containing 1 to 4 carbon atoms, an alkoxy radical containing 1 to 4 carbon atoms or the radical NO2, and
- (F) an amino group,
- (3) a phenyl group, optionally substituted with at least one of a halogen atom, an alkyl radical containing 1 to 4 carbon atoms or an alkoxy radical containing 1 to 4 carbon atoms,
- (4) a pyridylalkyl (containing 1 to 3 carbon atoms in the alkyl portion) group, optionally substituted with at least one of 1 halogen atom, an alkyl radical containing 1 to 4 carbon atoms or a cyano group,
- (5) an alkyl- or phenyl- or phenylalkylcarbonylalkyl group, each alkyl part of which contains 1 to 3 carbon atoms and the phenyl part of which is optionally substituted with 1 to 5 substituents chosen from a halogen atom, an alkyl radical containing 1 to 4 carbon atoms, an alkoxy radical containing 1 to 4 carbon atoms or the radical NO2, or
- (6) a trialkyl($C_1$–$C_4$)silylalkyl($C_1$–$C_4$) group, it being possible for the alkyl part to be substituted with a phenyl group which may be optionally substituted with an alkyl radical containing 1 to 4 carbon atoms;

Y is a hydrogen or halogen atom, an alkyl or alkoxy radical containing 1 to 4 carbon atoms; and n is an integer from 1 to 3, with the possibility that, when n is greater than 1, Y may be identical or different, on condition that, when Y is a hydrogen atom, R is not a hydrogen atom or a methyl or ethyl radical and when n is 3 and Y is a tert-butyl radical, R is not a tert-butyl radical.

2. The derivative according to claim 1, wherein, in formula I, R is an alkyl radical containing 1 to 8 carbon atoms or an alkenyl radical containing 2 to 4 carbon atoms.

3. The derivative according to claim 1, wherein, in formula I, Y is a hydrogen atom and R is an alkyl radical containing 3 to 8 carbon atoms, an alkenyl radical containing 2 to 4 carbon atoms, an alkoxycarbonylmethyl radical, an optionally substituted phenyl radical, an optionally substituted phenylcarbonylmethyl radical, or a pyridylmethyl radical.

4. The derivative according to claim 1 wherein said ammonium cation M is mono-, di-, or trisubstituted with a straight-chain or branched alkyl radical containing 1 to 18 carbon atoms, a cycloalkyl radical containing 3 to 6 carbon atoms or a hydroxyalkyl radical containing 1 to 3 carbon atoms.

5. A fungicidal composition which contains, as active substance, a fungicidally effective amount of at least one compound of formula:

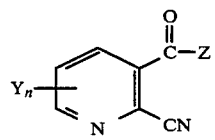

in which Z is either (1) a radical OR in which R is a hydrogen atom, alkali metal or alkaline with metal or optionally substituted ammonium or organic cation M, or (2) a straight-chain or branched alkyl radical containing 1 to 18 carbon atoms, or an alkenyl radical containing 2 to 18 carbon atoms, or an alkynyl radical containing 2 to 5 carbon atoms, it being possible for each of these radicals to be substituted with at least one of:
- (A) a halogen atom or a cyano group,
- (B) an alkoxy or alkylthio radical containing 1 to 4 carbon atoms,
- (C) a phenoxy radical, optionally substituted with at least one of a halogen atom, an alkyl radical containing 1 to 4 carbon atoms or an alkoxy radical containing 1 to 4 carbon atoms, and
- (D) a group COOR' or OCOR', in which R' is an alkyl radical containing 1 to 4 carbon atoms, an alkenyl radical containing 2 to 4 carbon atoms or a phenyl radical, (being optionally substituted with at least one of a halogen atom, an alkyl radical containing 1 to 4 carbon atoms or an alkoxy radical containing 1 to 4 carbon atoms), or a group I' of formula:

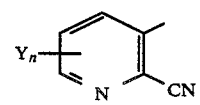

(I')

in which Y and n are as below,
- (E) a phenyl group, optionally substituted with at least one of a halogen atom, an alkyl radical containing 1 to 4 carbon atoms or an alkoxy radical containing 1 to 4 carbon atoms,
- (F) an amino group,
- (3) a pyridyalkyl (containing 1 to 3 carbon atoms in the alkyl portion) group, optionally substituted with at least 1 halogen atom or an alkyl radical containing 1 to 4 carbon atoms or a cyano group,
- (4) an alkyl- or phenyl- or phenylalkylcarbonylalkyl group, the alkyl part of which contains 1 to 3 carbon atoms and the phenyl part of which is optionally substituted with 1 to 5 substituents chosen from a halogen atom, an alkyl radical containing 1 to 4 carbon atoms, an alkoxy radical containing 1 to 4 carbon atoms or the radical NO2, and
- (5) a trialkyl ($C_1$–$C_4$) silylalkyl($C_1$–$C_4$) group, it being possible for the alkyl part to be substituted with a phenyl group which may be optionally substituted with 1 alkyl radical containing 1 to 4 carbon atoms;

Y is a hydrogen or halogen atom, an alkyl or alkoxy radical containing 1 to 4 carbon atoms;

and n is an integer from 1 to 3, with the possibility that, when n is greater than 1, Y may be identical or different.

6. The composition according to claim 5, wherein, in the formula, R is an alkyl radical containing 1 to 8 carbon atoms.

7. The composition according to claim 5, wherein, in the formula, R is a methyl or ethyl radical.

8. A method for the treatment of plants against fungal diseases, wherein a fungicidal composition according to one of claims 5, 6 or 7 is used in a fungicidally effective amount.

9. The composition according to claim 5 wherein said ammonium cation M is mono-, di- or trisubstituted with a straight-chain or branched alkyl radical containing 1 to 18 carbon atoms, a cycloalkyl radical containing 3 to 6 carbon atoms or an alkanoyl radical containing 1 to 3 carbon atoms.

* * * * *